Figure 1:
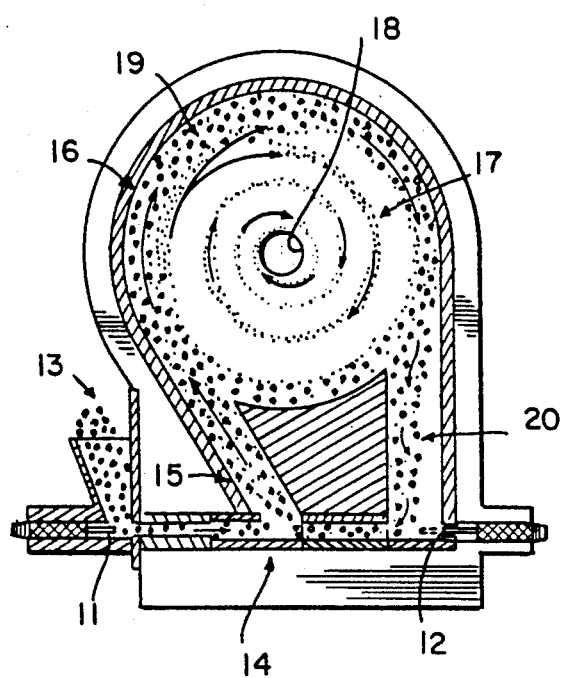
Figure 2:
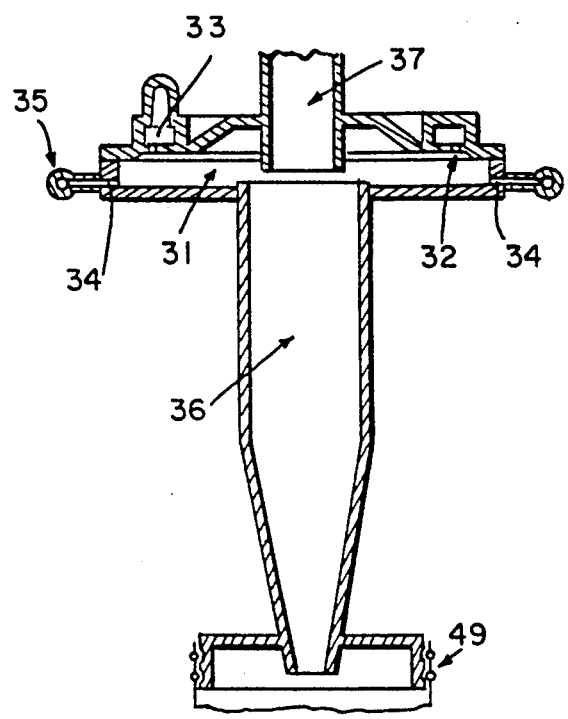
Figure 3:
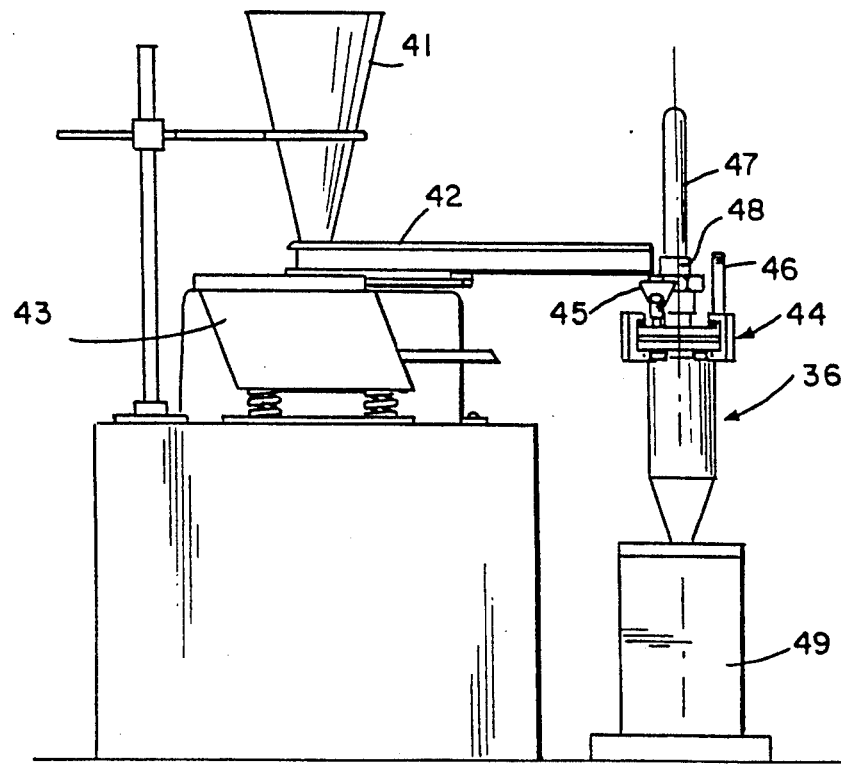

United States Patent [19]

Thompson

[11] Patent Number: 5,021,554

[45] Date of Patent: Jun. 4, 1991

[54] PROCESS FOR PROTEIN PARTICLE SIZE REDUCTION USING A FLUID-ENERGY MILL

[75] Inventor: William W. Thompson, Greenfield, Ind.

[73] Assignee: Eli Lilly and Company, Indianapolis, Ind.

[21] Appl. No.: 315,097

[22] Filed: Feb. 24, 1989

[51] Int. Cl.$^5$ .......................... C07K 15/14; C07K 3/00
[52] U.S. Cl. .................... 530/399; 530/395; 530/350; 514/21; 435/187
[58] Field of Search ................ 514/21; 530/399, 350, 530/395; 435/187

[56] References Cited

U.S. PATENT DOCUMENTS

| | | | |
|---|---|---|---|
| 3,965,086 | 6/1976 | Swain et al. | 530/377 |
| 4,681,752 | 7/1987 | Melillo | 424/453 |
| 4,801,456 | 1/1989 | Drengler | 424/422 |
| 4,837,202 | 6/1989 | Edwards et al. | 514/12 |

FOREIGN PATENT DOCUMENTS 177478 4/1986 European Pat. Off. .
61-236721 10/1986 Japan .

OTHER PUBLICATIONS

*Chemical Engineer's Handbook,* 8-43 to 8-44 (5th Ed. 1973, R. H. Perry & C. H. Chilton, editors).
*Crushing and Grinding,* George C. Lowrison, 263-266, (CRC Press, 1974).

Primary Examiner—Margaret Moskowitz
Assistant Examiner—Keith C. Furman
Attorney, Agent, or Firm—Kathleen R. S. Page; Leroy Whitaker

[57] ABSTRACT

The particle size of amorphous protein material is reduced to uniform particulates without protein decomposition or loss of activity by passing the material through a fluid-energy mill.

1 Claim, 1 Drawing Sheet

U.S. Patent — June 4, 1991 — 5,021,554

PROCESS FOR PROTEIN PARTICLE SIZE REDUCTION USING A FLUID-ENERGY MILL

BACKGROUND OF THE INVENTION

This invention relates to the field of formulation chemistry, and more particularly to the formulation of protein materials for subcutaneous injection.

A fluid product intended for subcutaneous injection should have a consistent viscosity and be homogeneous. Freeze dried proteins, such as recombinant bovine somatotropin and growth hormone releasing factor, are amorphous materials of variable and large flake size. The freeze drying process produces material that is not homogeneous. Bovine somatotropin and growth hormone releasing factor have useful biological activity when administered as parenteral injections, but to enable formulation of these materials as homogeneous, easily injectable products having a consistent viscosity, a method is needed for reducing the large amorphous protein flakes to uniform particulates. The size reduction process selected, in addition to being applicable to non-crystaline material, must also be practicable without protein decomposition or loss of potency, without water uptake, and without quantitative loss of material. The process should also lend itself to maintenance of sterile conditions.

SUMMARY OF THE INVENTION

This invention provides a process for reducing the particle size of protein material which comprises processing the materials in a fluid-energy mill. "Fluid-energy mill" refers to a fluid-energy or jet mill as described and illustrated in *Chemical Engineer's Handbook* 8-43 to 8-44 (5th ed. 1973, R.H. Perry and C.H. Chilton, editors) and in George C. Lowrison, *Crushing and Grinding,* 263-266 (CRC Press, 1974), which are incorporated by reference herein. In one class of such mills, the fluid energy is admitted in fine high-velocity streams at an angle at the periphery of a grinding and classifying chamber. Examples of suitable mills are TROST TM air impact pulverizers (Garlock Plastomer Products), illustrated in FIG. 1 and the MICRONIZER® mill (Sturtevant Mill Corp.), illustrated in FIG. 2. In another class of such mills, the fluid streams convey the particles at high-velocity into a chamber where two streams impact upon each other. In this class is the MAJAC® Jet Pulverizer (Majac, Inc.). What all fluid-energy mills have in common is that particle size reduction is achieved primarily by particles colliding with other particles, and not by contact between the particles and grinding surfaces of the mill. Although these types of milling equipment are well known and readily available, their particular utility for processing amorphous protein materials was not previously recognized.

BRIEF DESCRIPTION OF THE DRAWINGS

FIG. 1 is an elevation, in section, of a TROST TM air impact pulverizer suitable for use in this invention.

FIG. 2 is an elevation in section, of a MICRONIZER® mill suitable for use in this invention.

FIG. 3 is an elevation of equipment for carrying out the process of the invention.

DESCRIPTION OF THE PREFERRED EMBODIMENTS

The fluid-energy mill illustrated in FIG. 1 is a commercially available TROST TM mill. It uses opposing air or inert gas ($N_2$) streams which enter at two jets 11, 12. Material is fed into the mill at an inlet 13. The entering material is carried by the air stream from one jet 11 to an impact chamber 14, where particle size is reduced. The particles then travel through an upstack 15 to a centrifugal classification chamber 16, where the fine particles 17 collect in the center and exit the mill at an outlet 18. The larger, heavier particles 19 at the periphery of the classification chamber 16 return to the impact chamber 14 via a downstack 20, and their size is further reduced by impact with entering new material.

The mill illustrated in FIG. 2 is a commercially available MICRONIZER® mill. This mill has a shallow cylindrical grinding chamber 31. Eight feed inlets 32 are spaced around the periphery of the chamber. These inlets provide communication between the chamber and a feed manifold 33. A series of twelve air jets 34, which are supplied with air by an air manifold 35, are also spaced around the periphery of the grinding chamber. The air jets cause entering particles to move in high speed rotation, so that they violently impact each other. Larger particles are kept at the periphery of the grinding chamber, where most of the grinding occurs. Smaller particles are carried to the centrally located collector 36. Air escapes through a centrally located outlet 37.

FIG. 3 illustrates an arrangement of equipment suitable for carrying out the claimed process. The amorphous protein material is loaded into a feed cone 41, which opens at the bottom onto an inclined feed trough 42. The feed trough 42 is connected to a vibrator 43, which causes the material to move along the feed trough to the fluid-energy mill 44. In this case, the mill is one of the type illustrated in FIG. 2. The protein material passes from the trough through the inlet 45 of the mill. Air, which has preferably been filtered to sterilize it, is fed to the mill at an inlet 46. A filter bag 47 covers the fluid outlet 48 to prevent loss of material. Milled material is collected in a product collector 49 located under the mill. The collector may advantageously be a cyclone collector in which centrifugal acceleration is used to separate the milled product from the air.

One pass of protein material through a fluid-energy mill provides the desired improvement in product characteristics, but further passes are not harmful. The milled material is then ready to be formulated. A suitable formulation for milled recombinant bovine growth hormone is disclosed in U.S. Pat. Application Serial No. 06/768,605 filed Aug. 23, 1985.

The following Tables report particle size distribution data for three lots of BST before and after milling in accordance with the invention. In each case, the BST was passed a single time through a 2 inch diameter Trost TM air mill. Particle size was determined using a Malvern laser particle sizer (Malvern Instruments, Inc., 10 Southville Road, Southborough, Mass. 01772).

| | Before milling | After milling |
|---|---|---|
| | Lot 1 | |
| 50% less than | 164.5 microns | 6.1 microns |
| 90% less than | 673.0 microns | 11.3 microns |
| 10% less than | 27.8 microns | 2.8 microns |
| | Lot 2 | |
| 50% less than | 114.5 microns | 6.5 microns |
| 90% less than | 345.9 microns | 12.6 microns |

-continued

| | Before milling | After milling |
|---|---|---|
| 10% less than | 26.5 microns | 2.9 microns |
| | Lot 3 | |
| 50% less than | 103.3 microns | 5.7 microns |
| 90% less than | 313.8 microns | 9.3 microns |
| 10% less than | 25.3 microns | 2.8 microns |

The process of this invention has the following features and advantages:

1. There is no significant loss of potency of the milled material compared to unmilled material, because no heat is generated, and there is no product contamination from the milling process which could occur if the mill had abradable moving parts. This is advantageous for heat labile proteins.

2. The milling can readily be carried out under low moisture conditions. The air used in the process can be filtered dry, so that water uptake by hygroscopic proteins can be minimized. This is advantageous for water labile proteins.

3. The milling can readily be carried out under sterile conditions. The air used in the process can be sterilized, for example, by passing it through a 0.2 micron filter.

4. A high rate of recovery (over 95%) is typical.

5. The particle size of a non-crystalline protein can typically be reduced to less than 100 microns, as determined by scanning electron microscopy, Malvern laser particle sizer, or other suitable particle sizing techniques.

In contrast to fluid-energy mills, impact mills tend to smear non-crystalline protein products rather than reduce particle size. This smearing is potentiated by moisture uptake by the hygroscopic proteins. Further, the localized heat generated by impact mills causes protein degradation.

The milled protein material produced by the process of this invention has approximately double the bulk density of the freeze dried product before milling. This improves the handling characteristics of the bulk material. The milled material can be formulated to a homogeneous, consistent product for parenteral injection.

I claim:

1. A process for formulating a protein material selected from bovine somatotropin and growth hormone releasing factor as a parenteral product, which comprises (a) passing amorphous flakes of the protein material through a fluid-energy mill, and (b) admixing the milled material with a pharmacologically acceptable carrier or diluent.

* * * * *